(12) United States Patent
Witt

(10) Patent No.: US 12,151,127 B2
(45) Date of Patent: Nov. 26, 2024

(54) MASK AND METHOD FOR DEACTIVATING A PATHOGENIC AEROSOL

(71) Applicant: Marc Stefan Witt, Emeryville, CA (US)

(72) Inventor: Marc Stefan Witt, Emeryville, CA (US)

(73) Assignee: Denis Armand Pettee, Rotandas West, FL (US)

( * ) Notice: Subject to any disclaimer, the term of this patent is extended or adjusted under 35 U.S.C. 154(b) by 434 days.

(21) Appl. No.: 17/300,827

(22) Filed: Nov. 18, 2021

(65) Prior Publication Data
US 2022/0266070 A1  Aug. 25, 2022

Related U.S. Application Data

(63) Continuation-in-part of application No. 17/300,034, filed on Feb. 19, 2021, now Pat. No. 12,022,899.

(51) Int. Cl.
*A62B 23/02* (2006.01)
*A41D 13/11* (2006.01)

(52) U.S. Cl.
CPC .......... *A62B 23/025* (2013.01); *A41D 13/11* (2013.01)

(58) Field of Classification Search
CPC .............................. A62B 23/025; A41D 13/11
See application file for complete search history.

(56) References Cited

U.S. PATENT DOCUMENTS

2020/0179547 A1   6/2020   Choi

OTHER PUBLICATIONS

WO2018/033793A1. "Material, Device, and Method for Deactivating Pathogens in Aerosol, and Methods for Manufacturing Thereof" by Choi, Hyo-Jick. Feb. 22, 2018 (Year: 2018).*

* cited by examiner

*Primary Examiner* — Nirvana Deonauth
(74) *Attorney, Agent, or Firm* — John W. Carpenter

(57) ABSTRACT

A method for producing an improved mask or device for killing or deactivating pathogens, such as viruses. A mask or device produced in accordance with the method for producing. A method for killing, or making inviable, viruses, such as airborne viruses. A pathogen-deactivating assembly having two zones of hydrophilic particulate matter for deactivating a pathogenic aerosol. The two hydrophilic particulate matter zones are separated by a hydrophobic fibrous partition.

16 Claims, 14 Drawing Sheets

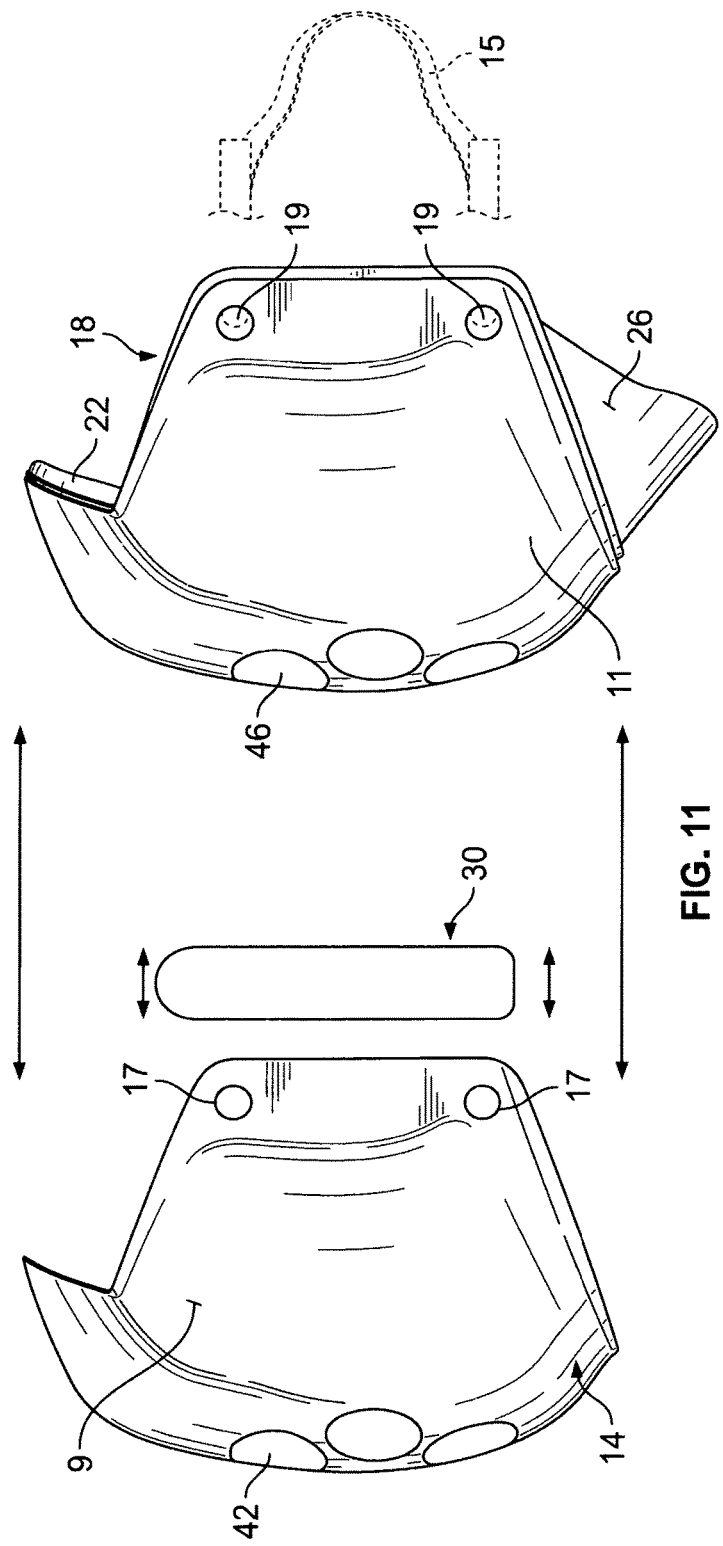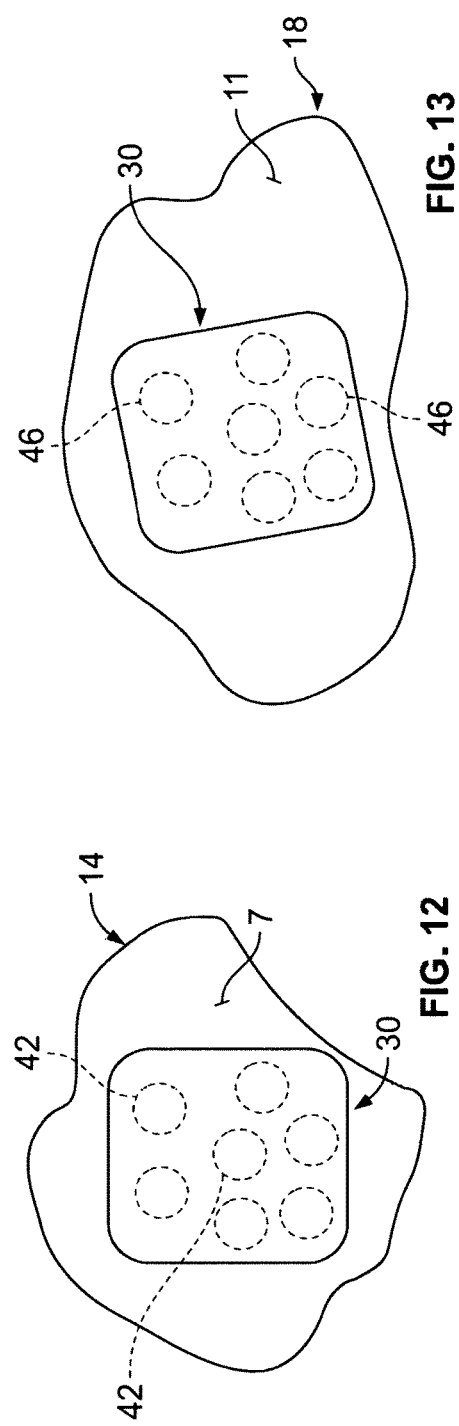
FIG. 11
FIG. 12
FIG. 13

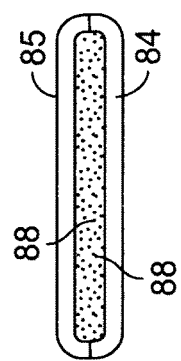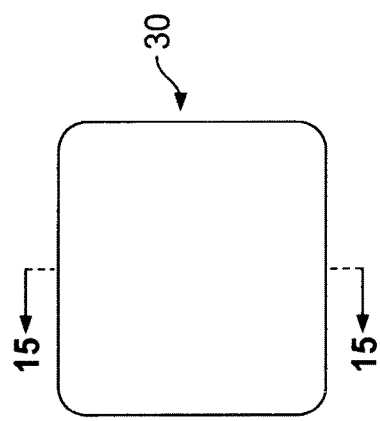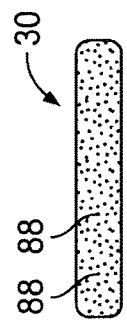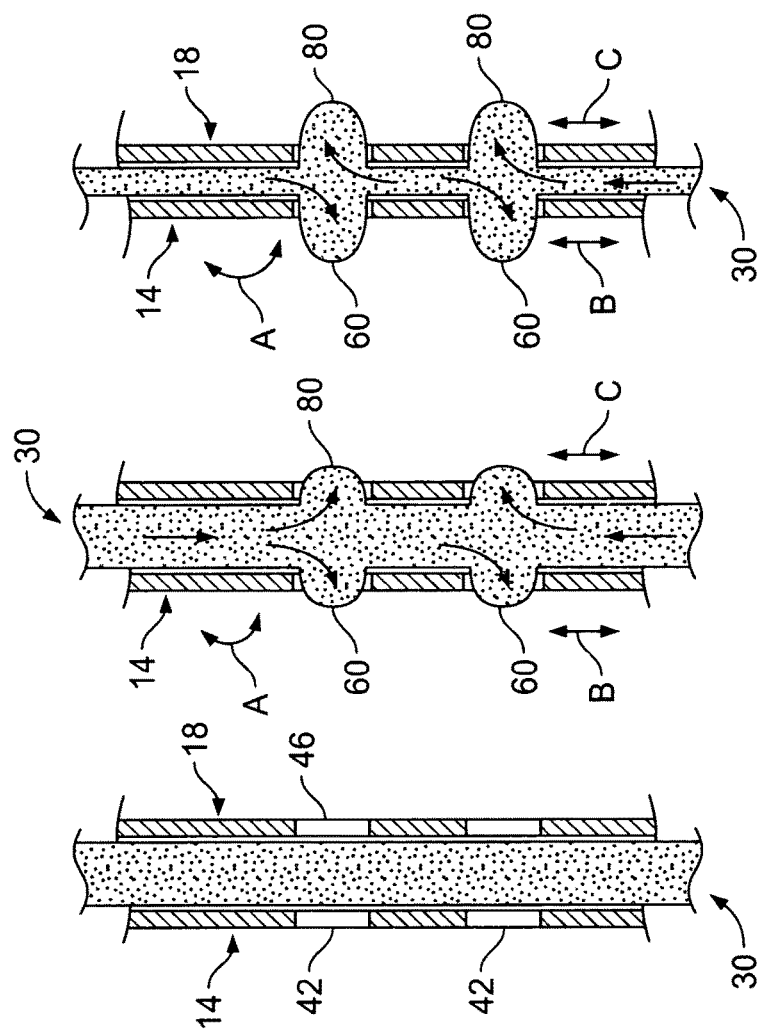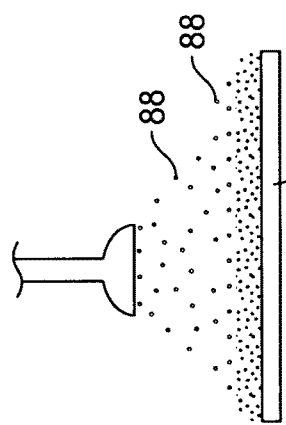

MASK AND METHOD FOR DEACTIVATING A PATHOGENIC AEROSOL

CROSS-REFERENCE TO RELATED APPLICATION

This is a continuation-in-part patent application of co-pending patent application having application Ser. No. 17/300,034, filed Feb. 19, 2021. Patent application Ser. No. 17/300,034 is fully incorporated herein by reference thereto as if repeated verbatim immediately herein. All benefits of the Feb. 19, 2021 filing date are claimed. Patent application Ser. No. 17/300,034 is a non-provisional, utility patent application related to Provisional Patent Application having application No. 63/100,762, filed Mar. 30, 2020, inventor Marc S. Witt, entitled "A Mask for Killing Viruses and Method." Provisional Patent Application having application No. 63/100,762, filed Mar. 30, 2020, is fully incorporated herein by reference thereto as if repeated verbatim immediately herein. All benefits of the Mar. 30, 2020 filing date for the Provisional Patent Application are claimed.

BACKGROUND OF THE INVENTION

1. Field of Invention

The present invention broadly relates in general to a device (preferably a mask) and method for producing a mask which eliminates pathogenic aero-solutions when worn. More specifically, embodiments of the present invention provide an improved mask and method for killing (or producing unviable) viruses, such as COVID-19 (the coronavirus disease caused by the SARS-CoV2 virus of 2019), H1N1 subtype in 1918, H2N2 subtype in 1957, and H3N2 subtype (Hong Kong flu) in 1968.

2. Description of the Background Art

The world is currently experiencing a pandemic from a coronavirus disease caused by the SARS-CoV2 virus of 2019, frequently referred to by the acronym as COVID-19. Respiratory infections are one of the leading causes of illnesses and death in the United States. These infections are typically transmitted when infectious or pathogenic aero-solutions (a suspension of fine solid particles or pathogen-containing fine liquid droplets in air) are inhaled by people. While vaccines can reduce illnesses and mortality, a major disadvantage of vaccines is the length of time to develop a vaccine, as well as the need to continually develop vaccines which address any genetic change in viruses resulting from antigenic drift.

Conventional, known air filter devices or mask have significant drawbacks, such as lack of efficacy in protecting against minute infectious aero-solutions, and leakage from insufficient sealing, as well as inefficiencies in killing viruses at various points on the mask where the thickness and/or the effectiveness of the filtering devices or mask are insufficient or inefficient in deactivating, killing or making inviable infectious, pathogenic laden aero-solutions which pass through the air filter devices or mask, especially when the wearer inhales.

U.S. Patent Application Pub. No. 2020/0179547 A1, application Ser. No. 16/326,187, published Jun. 11, 2020, to Choi broadly teaches generally deactivating, or substantially decreasing the viability, of pathogens, such as bacterium, fungi and virus. Choi more specifically teaches devices and methods for filtration of and deactivating airborne pathogens, as well as teaching pathogen deactivating materials, and filters for deactivating pathogen. Choi also more specifically teaches a method for manufacturing the pathogen deactivating materials for the filter, and a method for deactivating airborne pathogens. U.S. Patent Application Pub. No. 2020/0179547 A1, application Ser. No. 16/326,187, published Jun. 11, 2020, to Choi is fully incorporated herein as if repeated verbatim. The incorporation is for all purposes, such as being an integral part of the specification, and to support any claims. Choi discloses mask which would be inefficient in deactivating or making inviable pathogenic aerosols at various points or locations on the outside surface of the mask because of insufficient thickness of the mask and/or lack of effectiveness at the various points or locations in deactivating airborne pathogens.

What is needed and what has been invented is an inexpensive, highly effective improved device that deactivates, kills or makes inviable pathogens (e.g., viruses). What is further needed and what has been invented is an inexpensive, highly effective improved mask, and method, that deactivates, kills or makes inviable airborne pathogens (e.g., viruses) when worn. The mask allows people to go back to work and regain economic recovery for their societies.

SUMMARY OF EMBODIMENTS OF THE INVENTION

Embodiments of the present invention broadly provide a method for producing an improved mask or device for killing or deactivating pathogens, such as viruses. Embodiments of the present invention also include a mask or device produced in accordance with the method for producing. Embodiments of the present invention further provide a method for killing, or making inviable, viruses, such as airborne viruses.

Embodiments of the present invention more specifically provide a method for producing a mask which deactivates a pathogenic aerosol, comprising the steps of: (a) providing an outer face member having an inner surface and a structure defining at least one outer member opening; (b) providing an inner face member having an outer surface and a structure defining at least one inner member opening; (c) disposing a pathogen-deactivating assembly, which contains a pathogen-deactivating matter, against the inner surface of the outer face member such as to generally cover the at least one outer member opening; (d) disposing the outer surface of the inner face member against the pathogen-deactivating assembly such as to generally cover the at least one inner member opening; (e) forming an outer pathogen-deactivating pocket through the outer member opening; and (f) forming an inner pathogen-deactivating pocket through the inner member opening.

Embodiments of the present invention also more specifically provide a mask produced in accordance with the method for producing a mask.

Embodiments of the present invention further also more specifically provide a method for deactivating a pathogenic aerosol, comprising the steps of: (a) providing a mask having at least one outer pathogen-deactivating pocket and at least one inner pathogen-deactivating pocket; (b) passing a first pathogenic aerosol through the outer pathogen-deactivating pocket and the inner pathogen-deactivating pocket to produce a second pathogenic aerosol having a portion of pathogens in the first pathogenic aerosol deactivated, leaving residual pathogens in the second pathogenic aerosol; and (c) passing the second pathogenic aerosol containing the residual pathogens through the inner pathogen-deactivating pocket to deactivate at least a portion of the residual pathogens in the second pathogenic aerosol.

Another embodiment of the present invention features a method for improving the deactivation of pathogens in a pathogenic aerosol. The method comprises passing a first pathogenic aerosol matter containing an aqueous fluid through a first pathogen-deactivating zone to deactivate pathogens and produce a second pathogenic aerosol matter having residual aqueous fluid and residual pathogens. The method further comprises removing water from the residual aqueous fluid to produce a third pathogenic aerosol matter having residual pathogens and the residual aqueous fluid containing less water. The third pathogenic aerosol is subsequently passed into and through a second pathogen-deactivating zone to deactivate at least a portion of said residual pathogens. The removing of water from the residual aqueous fluid to produce a third pathogenic aerosol matter preferably comprises passing the second pathogenic aerosol matter through a hydrophobic fibrous member. Water is removed from the residual aqueous fluid to improve the ability for the second pathogen-deactivating zone to deactivate at least a portion of the residual pathogens. The second pathogen-deactivating zone becomes more efficient in removing pathogens. The concentration of pathogens in the fluid is increased.

The first pathogen-deactivating zone and the second pathogen-deactivating zone are separated by a hydrophobic fibrous member and are disposed between an outer face member and an inner face member of a mask assembly. A portion of the first pathogen-deactivating zone protrudes through at least one aperture in the outer face member, and a portion of the second pathogen-deactivating zone protrudes through at least one aperture in the inner face member. Each of the pathogen-deactivating zones are encapsulated in a fibrous member, preferably a hydrophilic fibrous member.

The aqueous fluid, by way of example only, comprises a fluid which includes lung fluid. Respiratory pathogens are typically transmitted via respiratory droplets containing lung fluid laden with infectious pathogens. The generation and transportation of (aqueous) respiratory fluid droplets are main processes in the transmission pathways of respiratory pathogens.

Vaccines only work against specific pathogens. The mask technology of the present invention potentially deactivates and makes inviable airborne viruses. When the wearer of the mask inhales, air containing pathogens passes through pathogen-killing particulate matter contained in protruding pockets of pathogen-killing particulate matter, producing unviable pathogens. The pathogen-killing particulate matter is disposed in outer protruding pockets and inner protruding pockets, all disposed through orifices in the mask.

When the wearer of the mask exhales, any residual air containing pathogens between a user's face and the mask passes through protruding inner mask pockets containing pathogen-killing particulate matter and kills or makes inviable the pathogens. In an embodiment of the invention, when the mask is worn for a period of time, pathogen-killing particulate matter in the outer pockets typically become less effective in killing viruses than the pathogen-killing particulate matter in the inner pockets. This typically results from incoming airborne pathogens (viruses) contact the pathogen-killing particulate matter in the outer pockets first, which gradually dilutes its initial effectiveness in killing pathogens compared to the particulate matter in the inner pockets which is last to contact incoming airborne pathogens.

Thus, a feature of the present invention is exhaling through the mask to kill airborne pathogens (viruses) contained in residual air positioned between the face and the inner mask face. Also, residual air between the wear's face and the inner mask face, in combination with exhaled air from the lungs, is warmer, which typically enables at times a more effective killing of the pathogens in the residual air. Without the inner protruding pockets of the pathogen-killing particulate matter the wearer of the mask is subject to being infected from the pathogens contained in the residual air.

These provisions, together with the various ancillary provisions and features which will become apparent to those skilled in the art as the following description proceeds, are attained by the assemblies, devices and methods of the present invention, preferred embodiments thereof being shown with reference to the accompanying drawings, by way of example only, wherein:

BRIEF DESCRIPTION OF THE DRAWINGS

FIG. 11 is a segmented side elevational view of the mask showing the outer face member and the inner face member separated from each other, and the pathogen-deactivating assembly separately disposed between the outer face member and the inner face member.

FIG. 12 is a partial rear elevational view of the inner surface of the outer face member showing the pathogen-deactivating assembly disposed over and covering the apertures of the outer face member.

FIG. 13 is a partial front elevational view of the outer surface of the inner face member showing the pathogen-deactivating assembly disposed over and covering the apertures of the inner face member.

FIG. 14 is a top plan view of an embodiment of the pathogen-deactivating assembly.

FIG. 15 is a vertical sectional view of the pathogen-deactivating assembly taken in direction of the arrows and along the plane of line 15-15 in FIG. 14.

FIG. 16a is a side elevational view of a particulate dispenser sprinkling particulate matter (i.e., a pathogen-deactivating substance) on a fibrous aero-permeable substrate material, in the process for producing or forming an embodiment of the pathogen-deactivating assembly.

FIG. 16b is a side elevational view after the particulate dispenser had sprinkled the particulate matter (i.e., a pathogen-deactivating substance) on the fibrous aero-permeable substrate material, and after a fibrous aero-permeable superstrate member had been imposed over the particulate matter supported on the aero-permeable substrate material, and after the perimetrical edges of the fibrous aero-permeable superstrate member had been sealed (preferably sealed by heat) to the perimetrical edges of the fibrous aero-permeable substrate material, producing or forming an embodiment of the pathogen-deactivating assembly.

FIG. 17 is a partial sectional view of the outer face member and the inner face member with the pathogen-deactivating assembly disposed (and sandwiched) between the outer face member and the inner face member, before the outer face member and the inner face member begin compressing the pathogen-deactivating assembly by (and when) moving towards each other (and/or optionally slightly sliding back and forth relatively to each other, or vibrating in combination, or rotating in combination, or moving in any desired or given direction in combination), causing the particulate matter within the pathogen-deactivating assembly to migrate or move towards the apertures of the outer face member and the inner face member to begin the formation of protruding pockets of pathogen-deactivating substance.

FIG. 18 is a partial sectional view of the outer face member and the inner face member with the pathogen-deactivating assembly disposed (and sandwiched) between the outer face member and the inner face member, as and while the outer face member and the inner face member are compressing the pathogen-deactivating assembly by moving towards each other (and/or optionally slightly sliding back and forth relatively to each other, or vibrating in combination, or rotating in combination, or moving in any desired or given direction in combination), showing the migration or movement (preferably progressive migration or movement) of the particulate matter within the pathogen-deactivating assembly towards the apertures of the outer face member and the inner face member and the beginning of the formation (preferably progressive formation) of protruding pockets of pathogen-deactivating substance.

FIG. 19 is a partial sectional view of the outer face member and the inner face member with the pathogen-deactivating assembly disposed (and sandwiched) between the outer face member and the inner face member, after the outer face member and the inner face member have essentially fully compressed the pathogen-deactivating assembly and have moved a portion of the particulate matter through the apertures of the outer face member and the inner face member, and have formed pockets of pathogen-deactivating substance which protrude through the apertures.

DETAILED DESCRIPTION OF EMBODIMENTS OF THE INVENTION

Figure 1:
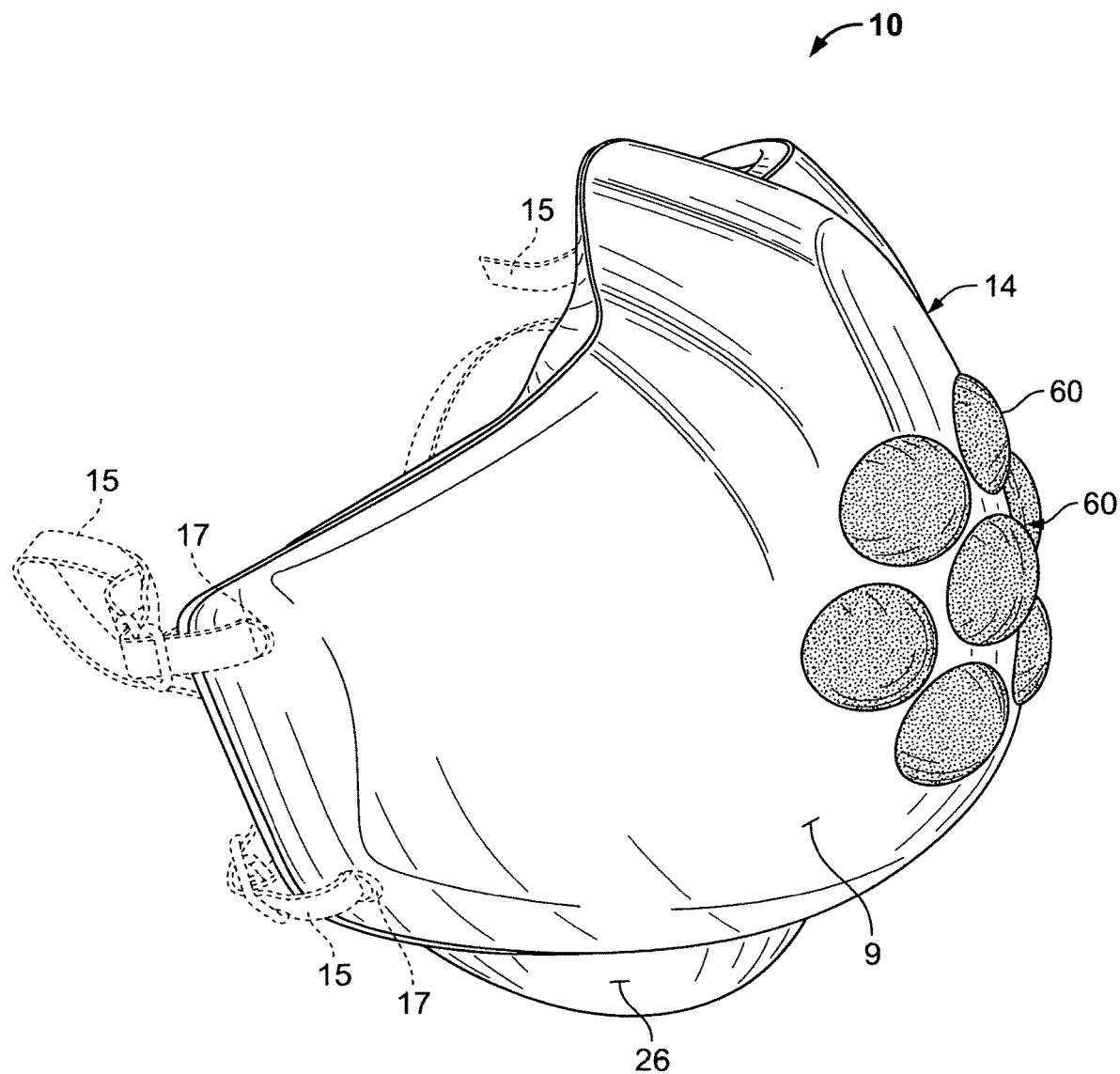
FIG. 1 is a front perspective view of an embodiment of the mask.
Figure 2:
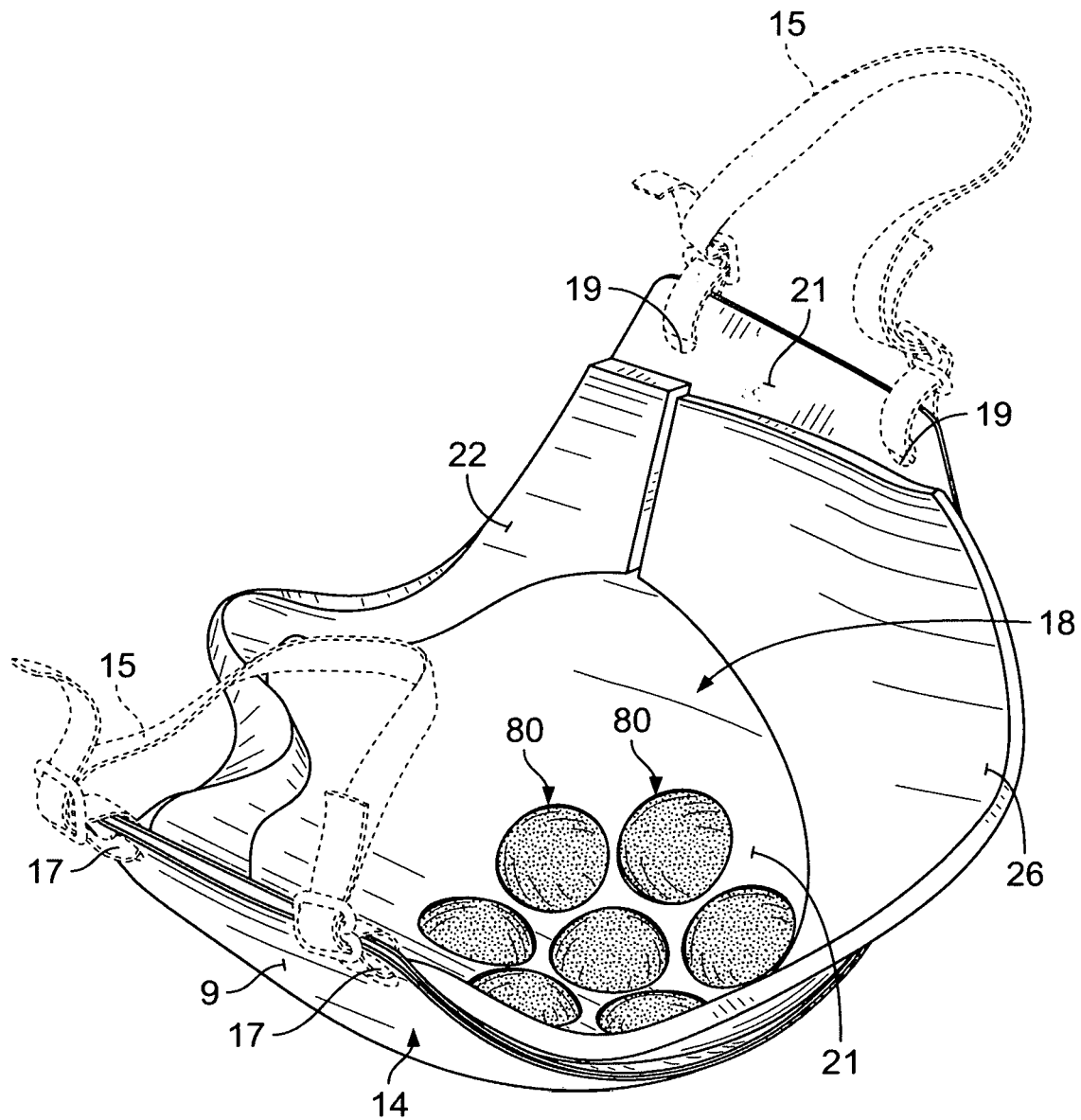
FIG. 2 is a rear perspective view of the embodiment of the mask.
Figure 3:
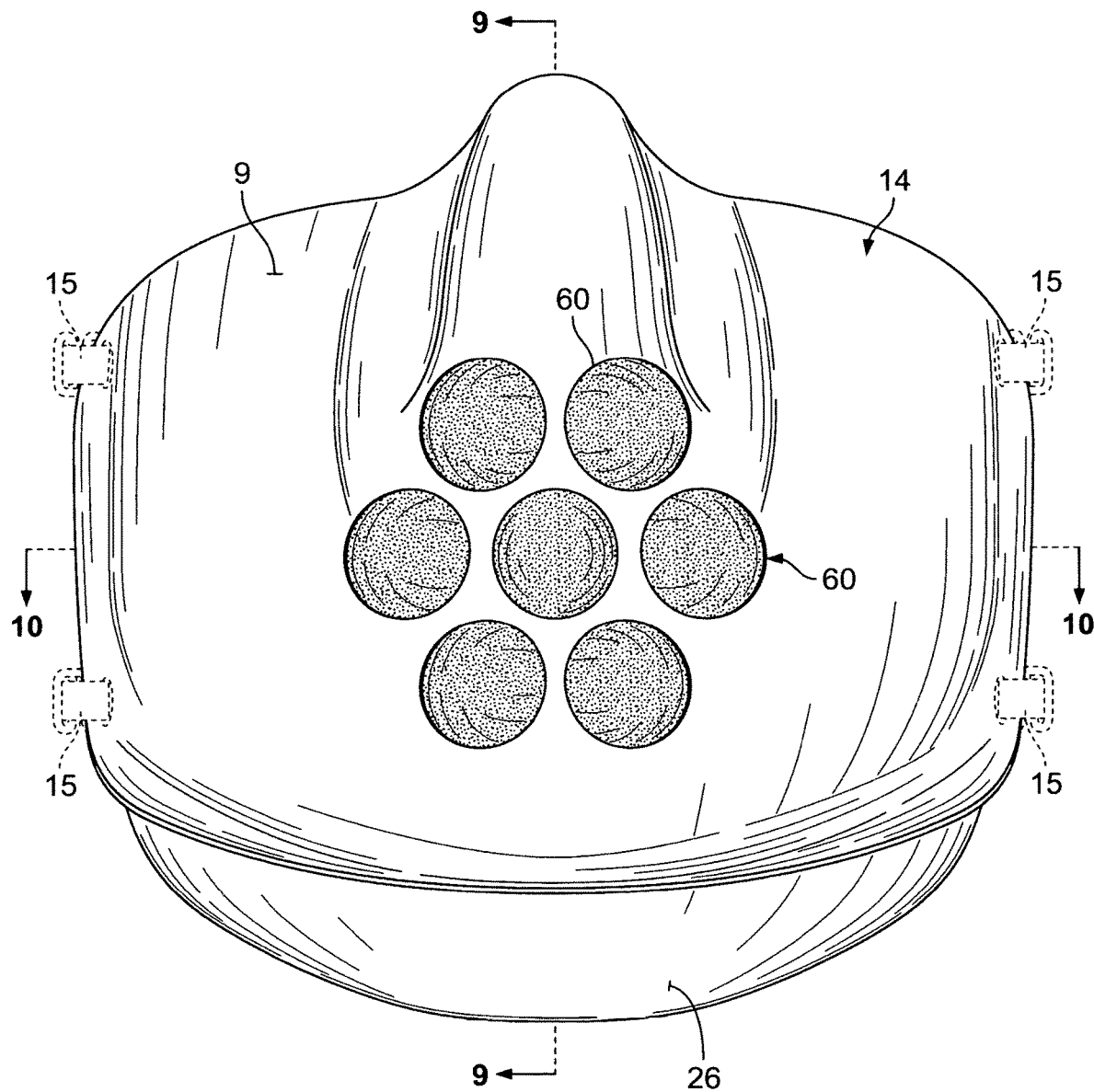
FIG. 3 is a front elevational view thereof.
Figure 4:
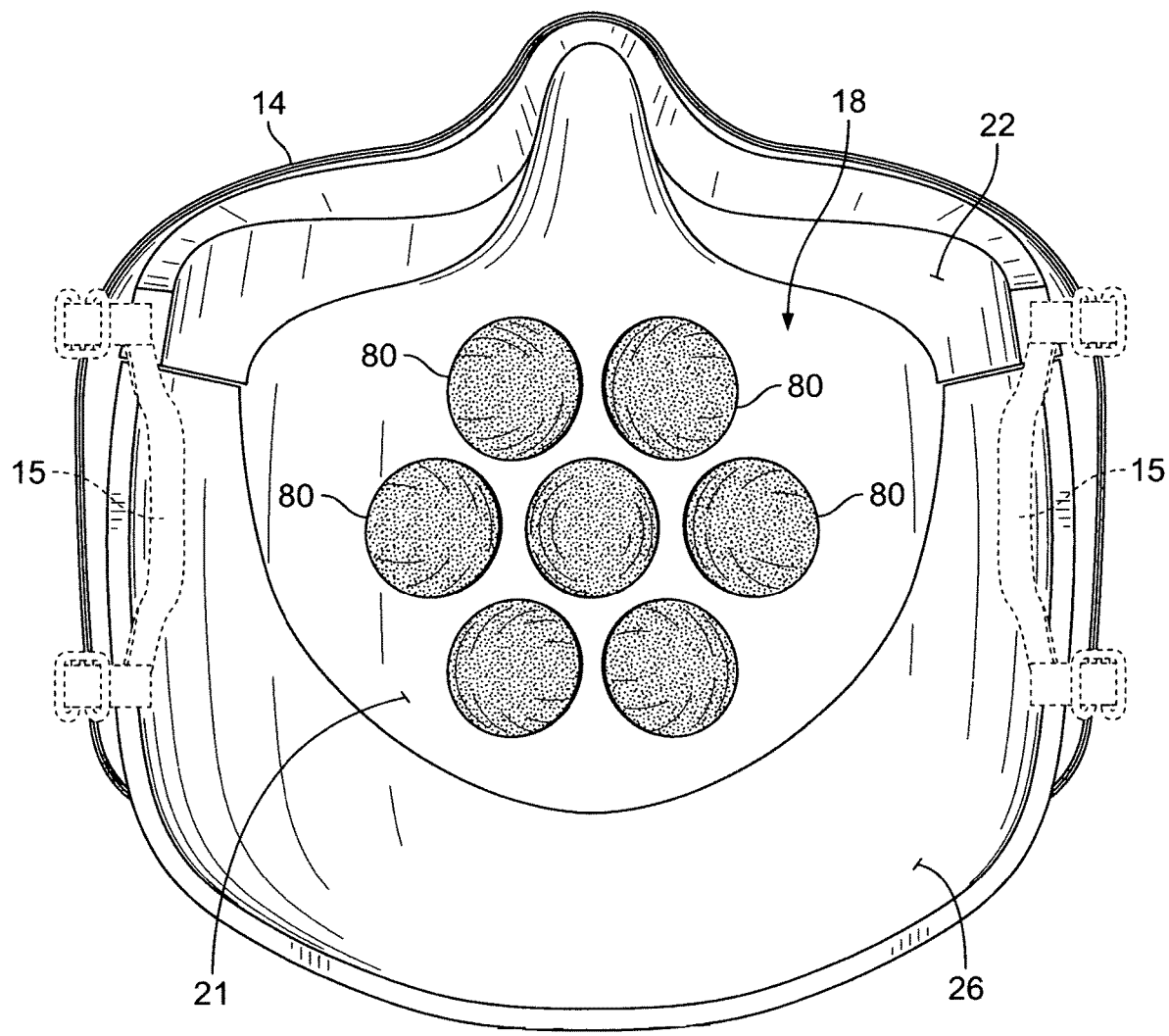
FIG. 4 is a rear elevational view thereof.
Figure 5:
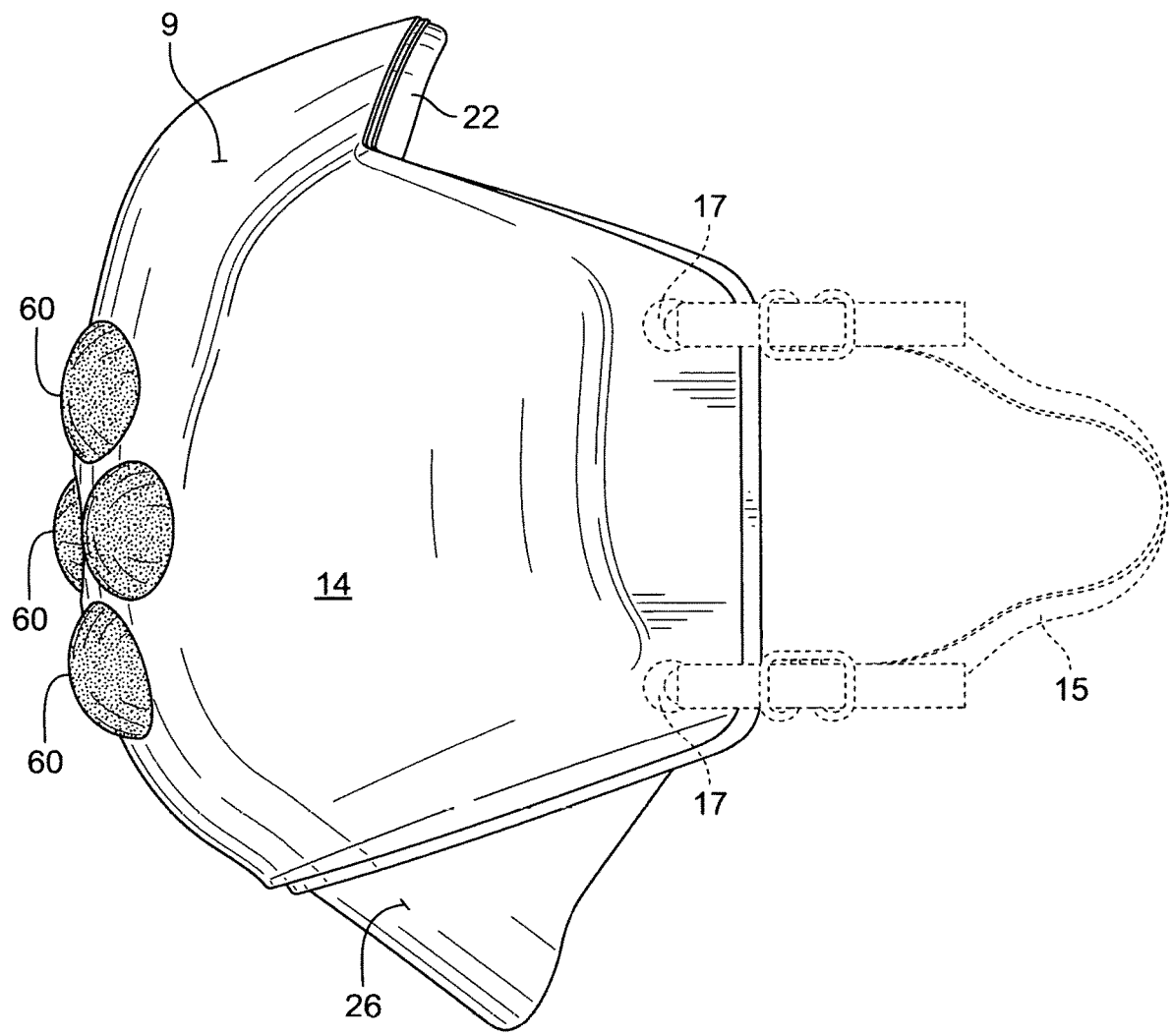
FIG. 5 is a right side elevational view thereof.
Figure 6:
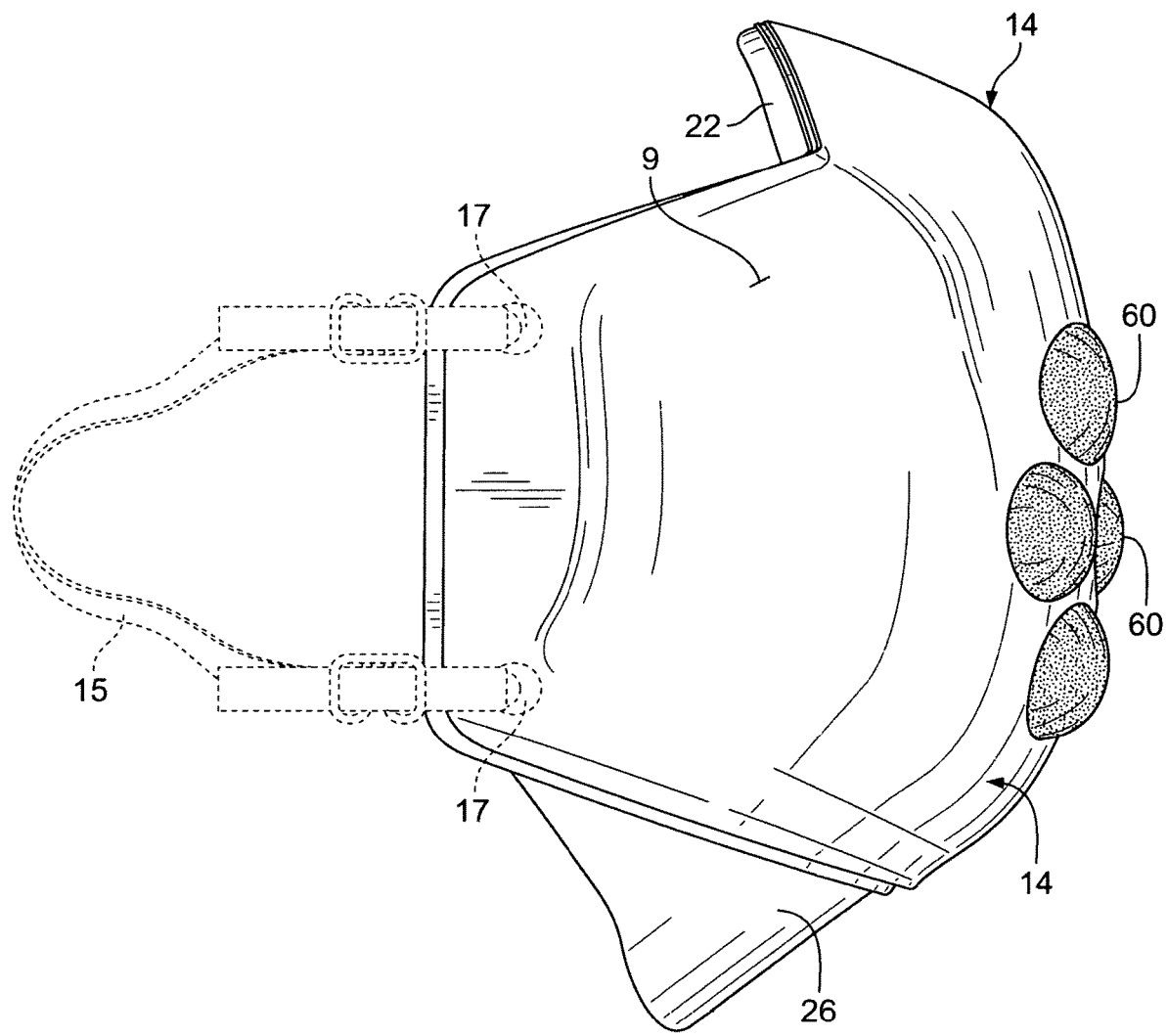
FIG. 6 is a left side elevational view thereof.
Figure 7:
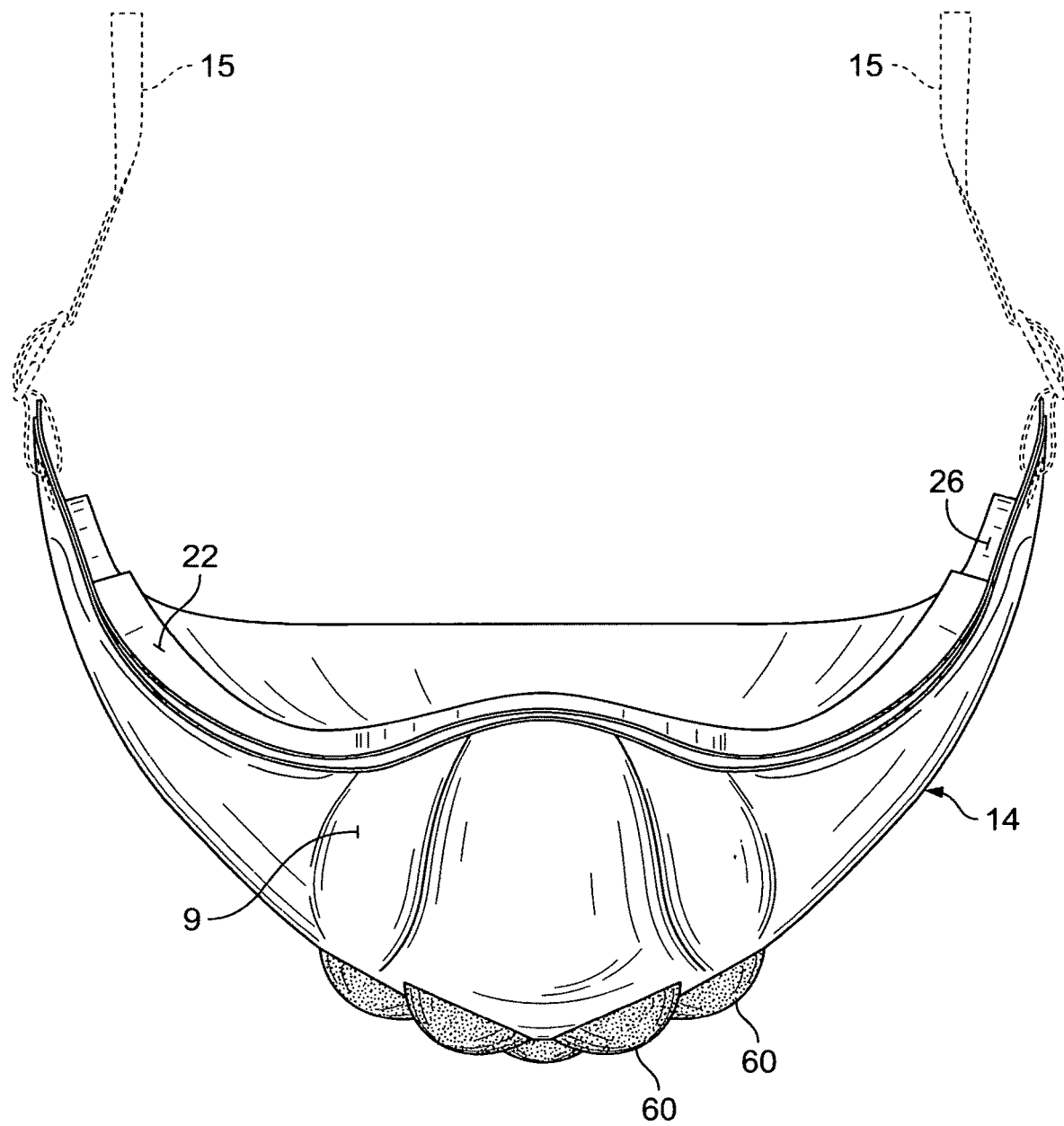
FIG. 7 a top plan view thereof.
Figure 8:
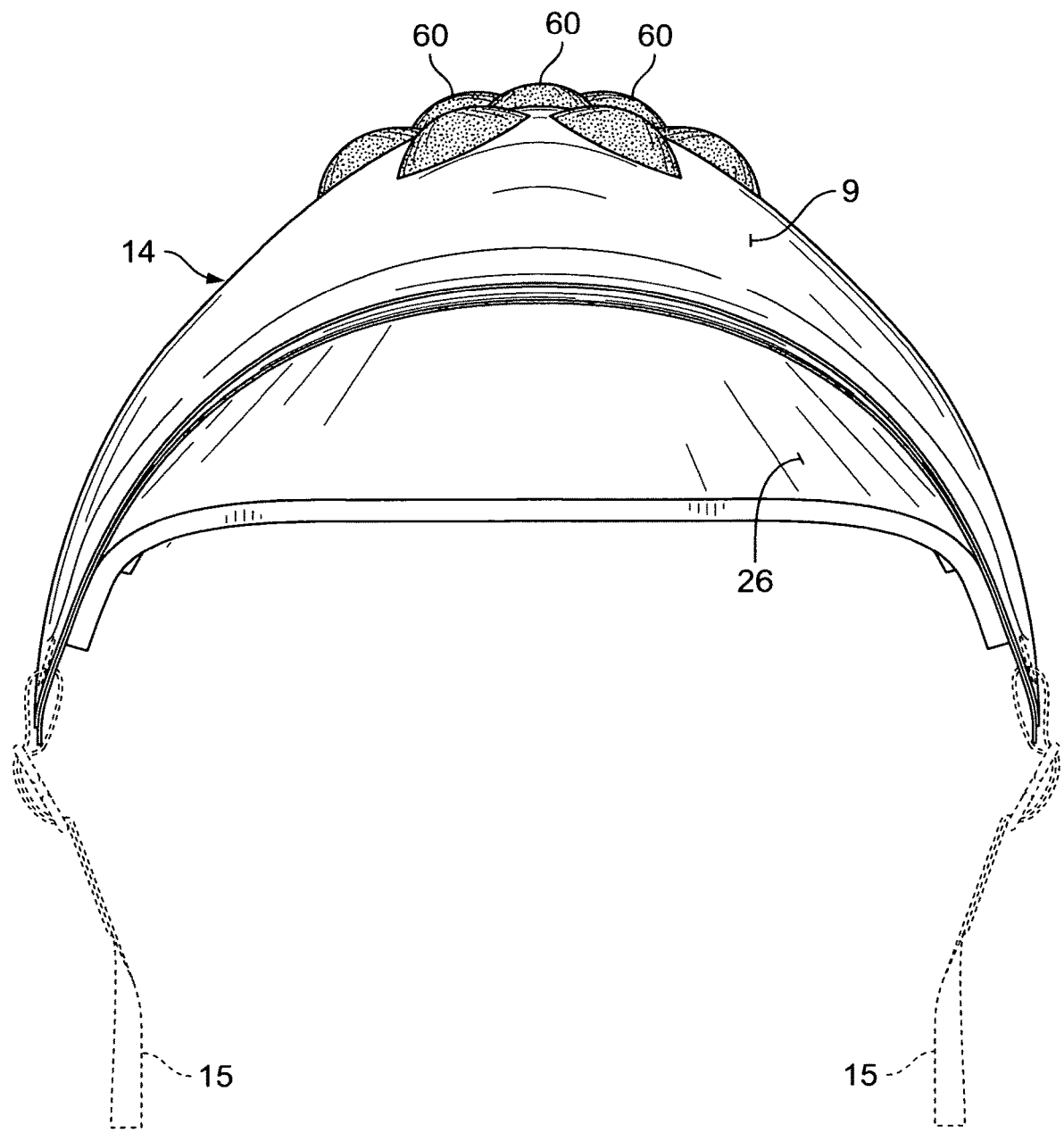
FIG. 8 a bottom plan view thereof.
Figure 9:
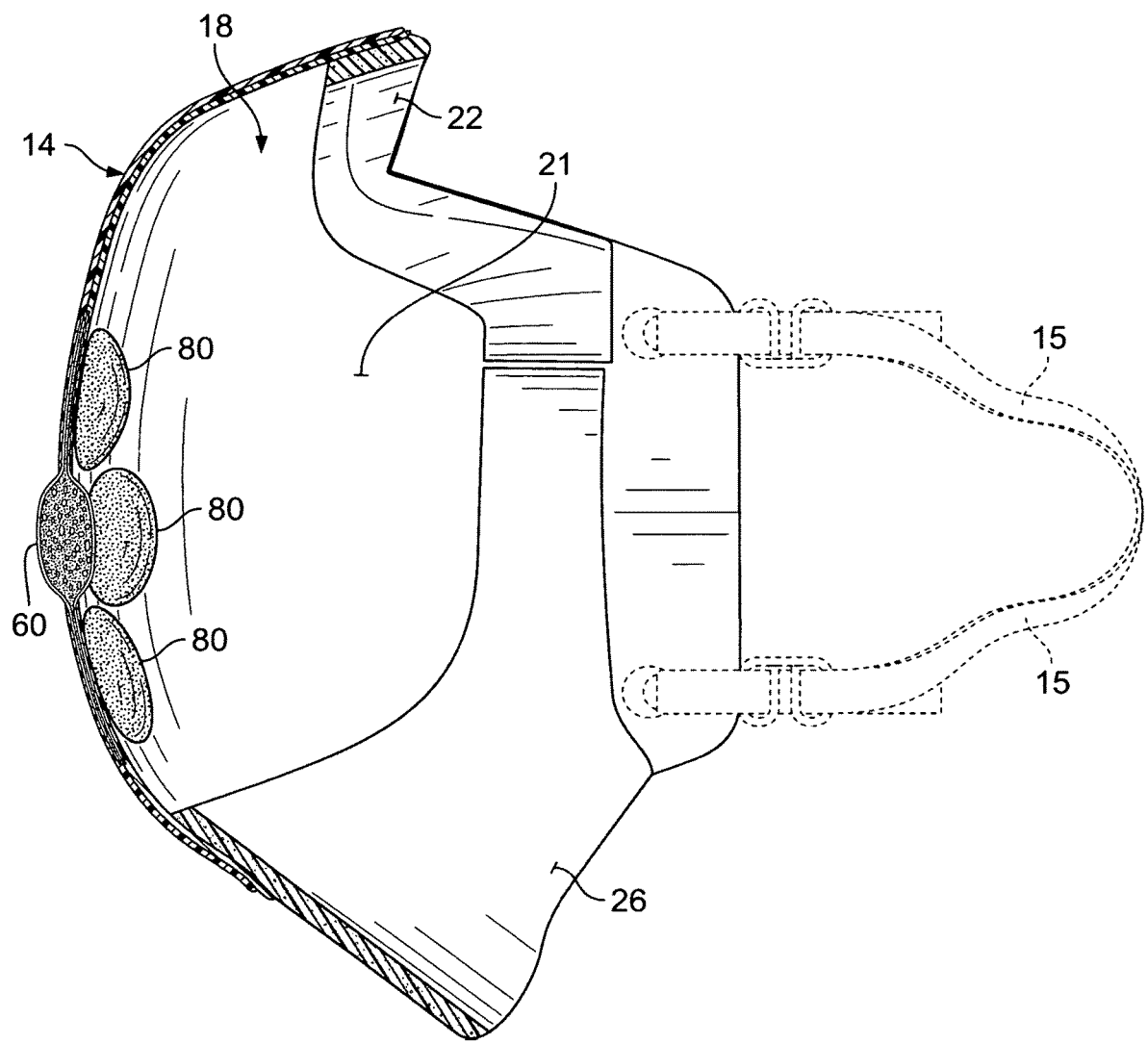
FIG. 9 is a sectional view taken in direction of the arrows and along the plane of line 9-9 in FIG. 3.
Figure 10:
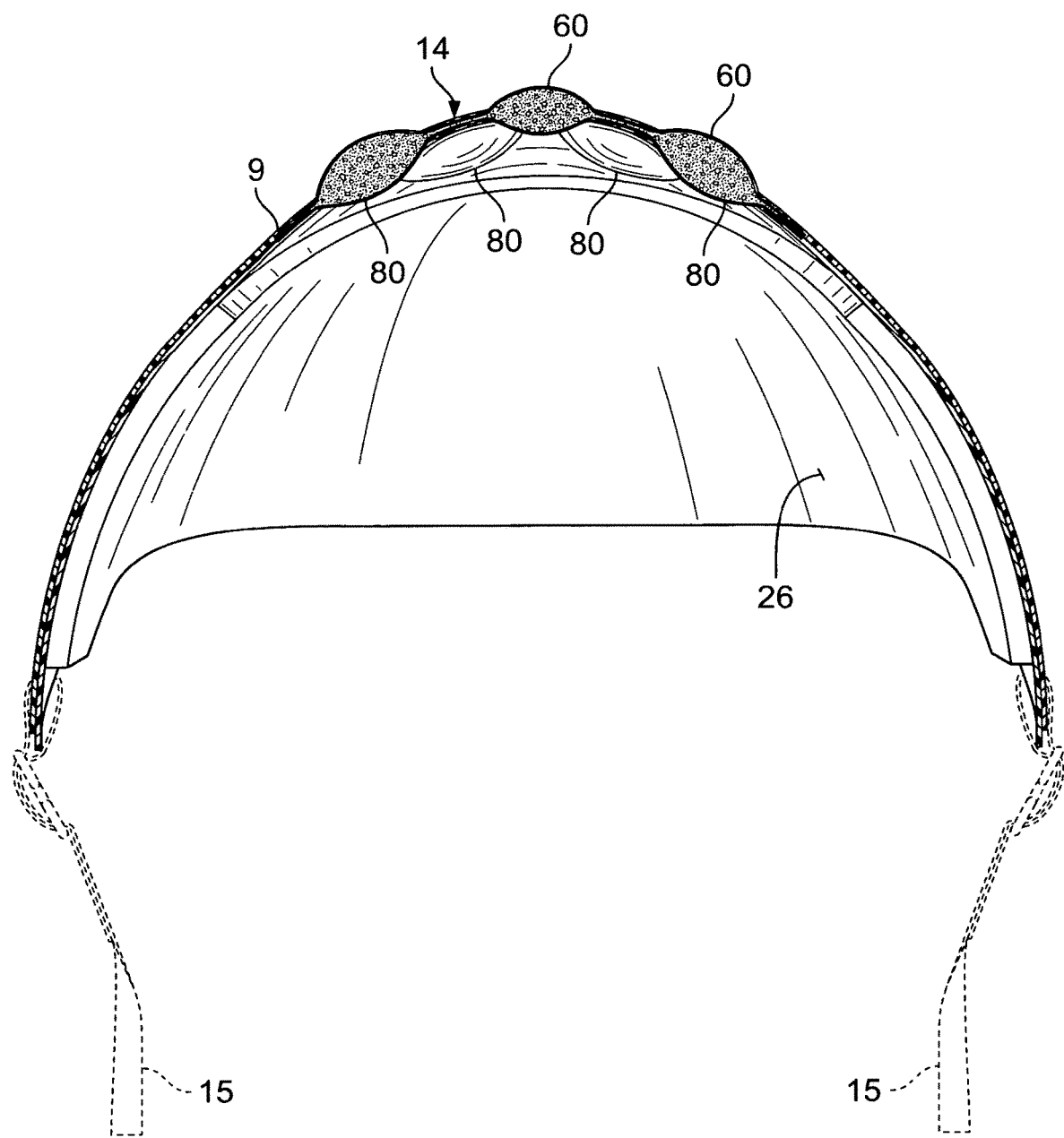
FIG. 10 is a sectional view taken in direction of the arrows and along the plane of line 10-10 in FIG. 3.

In the description herein for embodiments of the present invention, numerous specific details are provided, such as examples of components and/or methods, to provide a thorough understanding of embodiments of the present invention. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Referring in detail now to the drawings, wherein similar parts of embodiments of the present invention are identified by like reference numerals, there is seen a device, preferably a mask, generally illustrated as 10. The mask 10 has an outer face member 14 (or outer shell) and an inner face member 18 (or inner shell) releasably coupled or secured to the outer face member 14.

The inner face member 18 is configured to cover a wearer's nose and mouth. The outer face member 14 has an inner surface 7 and an outer surface 9, and is configured to fit over the inner face member 18. Ear straps 15-15 conveniently pass through apertures 17-17 and 19-19 in the outer face member 14 and the inner face member 18, respectively, and wrap around a wearer's ears for retaining the mask 10 on the wearer's face. The outer face member 14 and inner face member 18 have a plurality of apertures 42 and apertures 46, respectively. When the outer face member 14 and the inner face member 18 are coupled together, apertures 42 and 46 are generally aligned co-axially, sharing a common axis.

The inner face member 18 has an outer surface 11, and an inner surface 21 to which a nose bridge 22 and a facial bib member 26 are attached. The nose bridge 22 and facial bib member 26 may be manufactured from any material or substance which is comfortable for the wearer, such as by way of example epdm rubber or "foam," a composition of matter typically comprising polyols, polyisocyanates, water and other chemicals.

The inner face member 18 and the outer face member 14 may also be manufactured from any suitable material or substance for purposes of embodiments of the present invention, preferably a material or substance which is sturdy and strong enough to allow compression and/or otherwise movement of members 14, 18, and to cause and allow migration or movement (preferably progressive migration or movement) of the particulate matter 88 within the pathogen-deactivating assembly 30 towards the apertures 42 and 46 of the members 14 and 18 to form protruding pathogen-deactivating-substance pockets 60 and 80 (as illustrated in FIGS. 18 and 19). Suitable materials for producing members 14 and 18 include thermo-formed polystyrene, and plastics, such as by way of example only, polypropylene, polyethylene, and PVC.

A pathogen-deactivating assembly, generally illustrated as 30, is removably disposed between the outer face member 14 and the inner face member 18. The pathogen-deactivating assembly 30 may be easily removed or replaced after separating or decoupling the outer face member 14 from the inner face member 18. In a preferred embodiment of the invention, the pathogen-deactivating assembly 30 may resemble a tea bag. Preferably, the pathogen-deactivating assembly 30, as best shown in FIG. 16*b*, comprises a substrate 84, a superstrate 85 perimetrically connected to the substrate 84, such as by heat-sealing, with pathogen-deactivating particulate matter 88 (e.g., a salt crystal) contained within the secured borders or perimeters of substrate 84 and superstrate 85.

The protruding pathogen-deactivating-substance pockets 60 and 80 (as illustrated in FIGS. 18 and 19) provide an immediate larger quantity and/or volume of particulate matter 88 available for killing pathogens (or viruses), compared to where or when no protruding pockets exist, such as best shown in FIG. 17. The average surface area of particles of the particulate matter 88 agglomerated together should be tailored such as to generally maximize the pathogen-deactivating ability or quality of the particulate matter 88, while maintaining suitable and sufficient aero-permeability for pathogen-infected air. Surface area is a means by which particulate matter 88 interacts with its surrounding environment, whether the environment is a gas or a liquid. As particle size of the particulate matter 88 decreases, the surface area per unit volume (or mass) increases.

Specific surface area of the particles of particulate matter 88 may be defined as the total surface area of the particles (e,g., such as that contained in the respective protruding pathogen-deactivating-substance pockets 60 and 80) per unit of mass or weight. In a preferred embodiment of the invention, the total surface area of the particles of particulate matter 88 preferably ranges from about 1.0 $m^2/g$ to about 500.00 $m^2/g$, more preferably from about 20.00 $m^2/g$ to about 300.00 $m^2/g$, most preferably from about 30.00 $m^2/g$ to about 100.00 $m^2/g$.

In a preferred embodiment of the invention the particles of particulate matter 88 comprise a salt crystal including one or more of sodium, potassium, chloride, magnesium, sulfate, ammonium, phosphate, glutamate, tartrate, and their ions. More preferably, the particles of particulate matter 88 comprise either sodium chloride or potassium chloride, or a mixture of sodium chloride or potassium chloride, with the particles including a total surface area ranging from about 50.0 $m^2/g$ to about 500.00 $m^2/g$, more preferably from about 100.00 $m^2/g$ to about 300.00 $m^2/g$.

Substrate 84 and superstrate 85 may be manufactured from any suitable material or substance for purposes of embodiments of the present invention, preferably a material or substance which has sufficient aero-permeability allowing pathogen-infected air to pass through and into the particulate matter 88 for deactivating pathogens, and to enable the same air (including deactivated pathogens) to pass out of the assembly 30.

Substrate 84 and superstrate 85 are preferably manufactured of a material or substance which produces substrate 84 and superstrate 85 as having physical structural characteristics possessing sufficient flexibility and elasticity, such that when the outer face member 14 and the inner face member 18 compress the particulate matter 88 (contained within the combined substrate 84 and superstrate 85), and/or simultaneously (optionally) with slightly sliding back and forth relatively to each other (as reflected by arrows B and C in FIGS. 18 and 19), or vibrating in combination, or rotating in combination, or moving in any desired or given direction (e.g., shaking) in combination (as reflected by arrows A in FIGS. 18 and 19); the migration or movement of the particulate matter 88 (contained within the combined substrate 84 and superstrate 85) occurs towards the respective apertures 46 and 42 of the outer face member 18 and the inner face member 14, to eventually form protruding pathogen-deactivating-substance pockets 60 and 80 (as illustrated in FIGS. 18 and 19).

In a preferred embodiment substrate 84 and superstrate 85, and the pathogen-deactivating assembly 30, may be manufactured from one of either woven polyester fabric, non-woven polypropylene fabric, cellulose or nylon. The substrate 84 and superstrate 85, and the pathogen-deactivating assembly 30, may also be made of, or manufactured from, any of the pathogen-deactivating fibrous materials (identified therein by way of example fibrous material 100 or 200 or 700), or any of the multilayer structures (identified therein as "structure 300"), all disclosed in U.S. Patent Application Pub. No. 2020/0179547 A1, application Ser. No. 16/326,187, published Jun. 11, 2020, to Choi, entirely incorporated herein.

As shown in the drawings, the mask 10 for killing viruses includes the inner face member 18 (e.g., an inner shell) and the outer face member 14 (e.g., an outer shell) removably secured to the inner face member 18 (or inner shell). The inner and outer face members 18 and 14 (or inner and outer shells) have openings or apertures 46 and 42, respectively, wherethrough air may pass when a person, wearing the mask 10, breathes, i.e. inhales and exhales. Between the inner and outer face members 18 and 14 (or inner and outer shells) is the pathogen-deactivating assembly 30 (including particulate-matter filter elements) which may be removed therefrom as desired. The particulate-matter filter elements disposed within the pathogen-deactivating assembly 30 (e.g., a filter-containing assembly) kills viruses when the person wearing the mask breathes in (inhales) and breathes out (exhales). In a preferred embodiment of the invention, there are no poppet valves (air is exhaled and inhaled through the same particulate-matter filter elements). When air passes through the particulate-matter filter elements, the virus (or any pathogen) is killed or made inviable.

The filter elements may be, or include, or consist of, any suitable means or chemicals for killing viruses when a person breathes. There are a wide variety of chemical, electrical, photo, and other exposures that kill viruses. The selected materials must be harmless to the user, and completely effective in killing viruses during use. Representative means, materials or chemicals include one or more of the following: wet emulsions; acid filters; alkaline filters; solvents; electro static exposure; electro chemical exposure; UV light exposure; and high temperature.

In a preferred embodiment of the invention, the filter element comprises, or includes, a material which includes, or consists of, a crystalline molecular structure possessing hard sharp molecular corners or edges for killing the virus, or rendering the virus unviable. It is known that a virus is an infective agent that typically consists of a nucleic acid molecule (e.g., DNA, RNA) in a protein coat. The crystalline molecular structure may be any molecular structure having sharp corners for engaging and piercing the protein coat (capsid) of the virus, causing the virus to become incapacitated.

In a preferred embodiment of the invention, the filtering (pathogen killing) material comprises an alkali metal chloride, preferably sodium chloride or potassium chloride. More preferably, the material includes a crystalline molecular structure possessing hard sharp molecular corners or edges is sodium chloride, such as salt crystals sold under the product name Morton Salt. Sodium chloride crystals are typically cubic in form, comprising tiny cubes tightly bound together through ionic bonding of the sodium and chloride ions.

The filtering elements design may include dry salt crystals encapsulated in a (2) layers of filter paper (assembled like a tea bag). When fluid droplets (e.g., saliva, mucous) containing a virus deposits or resides on the filter element(s) (or in pathogen-deactivating assembly 30), the fluid droplet absorbs the salt. Air from a person breathing in and out evaporates the fluid droplet, leaving the virus in an inviable form, along with crystallized salt.

Air born viruses are typically carried in moisture droplets from a host. The virus particles are suspended in water droplets in the air surrounding an infected person. When this aerosolized pathogen mixture makes contact with the virus killing filter pathogen-deactivating assembly 30, the virus is destroyed due to the chemical/physical interaction with the pathogen-deactivating assembly 30 (e.g., a filter cartridge). If sodium chloride is used in the pathogen-deactivating assembly 30, then the water born virus bonds to the salt, as an impurity in the water salt mixture. After the water has the opportunity to evaporate (assisted by the inhaling and exhaling of air by the user—exhaled air is warm), the salt crystal regrows, encapsulating the virus particle. The virus is then "trapped" during the "recrystallization period" as an "impurity" in the lattice structure of the crystal. The virus is chemically dissolved by the salt due to chemical reactions at the surface of the virus shell. This chemical exposure causes the destruction of the virus shell. The virus is made inactive or destroyed, due to its direct contact with salt and saline solutions.

As previously indicated, there are other chemicals that can offer virus killing reactions, that are available to be integrated into the pathogen-deactivating assembly 30. Embodiments of the present invention provide a suitable method to hold the virus killing particulate filter elements. Special considerations are given to there being, an effective face seal, low cost production, fast assembly, two directional killing (e.g., flow of air from inhaling and exhaling), comfort, and immediate participation with society, even if the person wearing the device is infected or is in an environment with infected people.

Continuing to refer to the drawings for describing an embodiment of the invention comprising a method for producing a device (e.g., the mask 10), including its associated protruding pathogen-deactivating-substance pockets 60 and 80 (as illustrated in FIGS. 18 and 19), initially, the pathogen-deactivating assembly 30 is obtained or produced. In a preferred embodiment, the pathogen-deactivating assembly 30 may be produced by randomly sprinkling or otherwise disbursing or distributing a particulate salt crystal (e.g., pathogen-deactivating particulate matter 88) onto a suitable substrate, such as fibrous aero-permeable substrate member 84, as illustrated in FIG. 16a, insuring there is no or minimal coagulation of any salt crystal. After the desired amount of particulate salt crystal has been distributed as such, a suitable superstrate, such as the fibrous aero-permeable superstrate member 85 had been is imposed over the particulate matter supported on the aero-permeable substrate material 84, and after the perimetrical edges of the fibrous aero-permeable superstrate member 85 had been sealed (preferably sealed by heat) to the perimetrical edges of the fibrous aero-permeable substrate material 84, producing or forming an embodiment of the pathogen-deactivating assembly 30 (see FIG. 16b).

After the pathogen-deactivating assembly 30 has been obtained or produced, assembly 10 is disposed against the inner surface 21 of the outer face member 14, such as to fully cover the apertures 42 of the outer face member 14, as illustrated in FIG. 12. Subsequently, the outer surface 11 of the inner face member 18 is disposed against the assembly 10, such as to fully cover the apertures 46 of the inner face member 18, as illustrated in FIG. 13. After the assembly 30 has been disposed as such between the outer face member 14 and the inner face member 18 (see FIG. 17 which illustrates assembly 30 being disposed between the outer face member 14 and the inner face member 18), the outer face member 14 and the inner face member 18 begin compressing (or pressurizing) the particulate matter 88 contained within assembly 30, commencing the migration or movement of the particulate matter 88 towards the respective apertures 46 and 42 of the outer face member 18 and the inner face member 14, along with the moving and/or expanding of the layers (e.g. substrate 84 and superstrate 85) of the assembly 30 through apertures 46 and 42. This starts the process for forming the protruding pathogen-deactivating-substance pockets 60 and 80 (as best illustrated in FIG. 18). The compressing (or pressurizing) of the particulate matter 88, and/or the desired directional movements of the outer face member 18 and the inner face member 14 are continued until the outer face member 14 and the inner face member 18 have essentially fully compressed the pathogen-deactivating assembly 30 and have moved a portion of the particulate matter 88 through the apertures 46 and 42 of the outer face member 18 and the inner face member 14, and formed pockets 60 and 80 of pathogen-deactivating substance which protrude through the apertures 42 and 46 (as best illustrated in FIG. 19).

Figure 20:
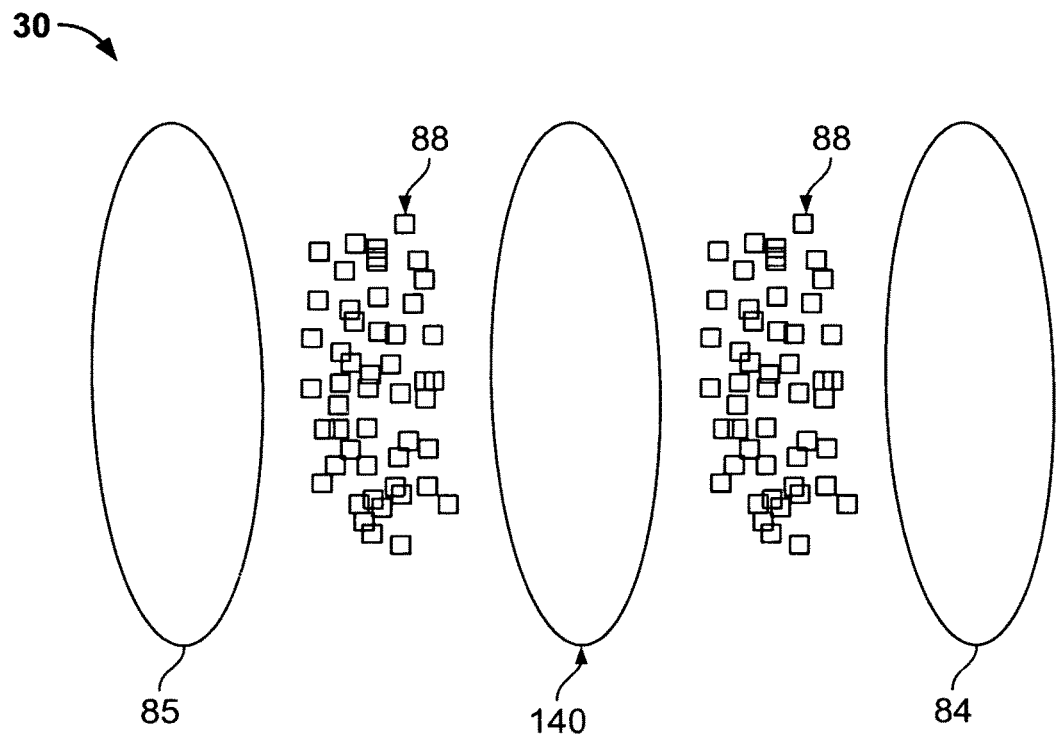
FIG. 20 is a segmented exploded view of another embodiment of the pathogen-deactivating assembly, illustrating an intermediate hydrophobic fibrous member (e.g., a fibrous member possessing poor water absorbency characteristics and comprising synthetic fibers such as nylon, acrylic and modacrylic) disposed between a pair of outer fibrous members, with particulate matter (e.g., hydrophilic particulate matter with pathogen-deactivating ability or quality) positioned between one of the outer fibrous members and the intermediate hydrophobic fibrous member. and between the other outer fibrous member and the intermediate hydrophobic fibrous member.

Referring now to FIGS. 20-24 for another embodiment of the invention, there is seen in FIG. 20 a segmented exploded view of another embodiment of the pathogen-deactivating assembly 30 comprising substrate 84 (e.g., a fibrous member having sufficient aero-permeability) and superstrate 85 (e.g., also a fibrous member having sufficient aero-permeability), along with an intermediate member 140 (preferably a fibrous hydrophobic intermediate member having sufficient aero-permeability) disposed between substrate 84 and superstrate 85 and separated from substrate 84 and superstrate 85 by the particulate matter 88 (e.g., a salt crystal).

Figure 21:
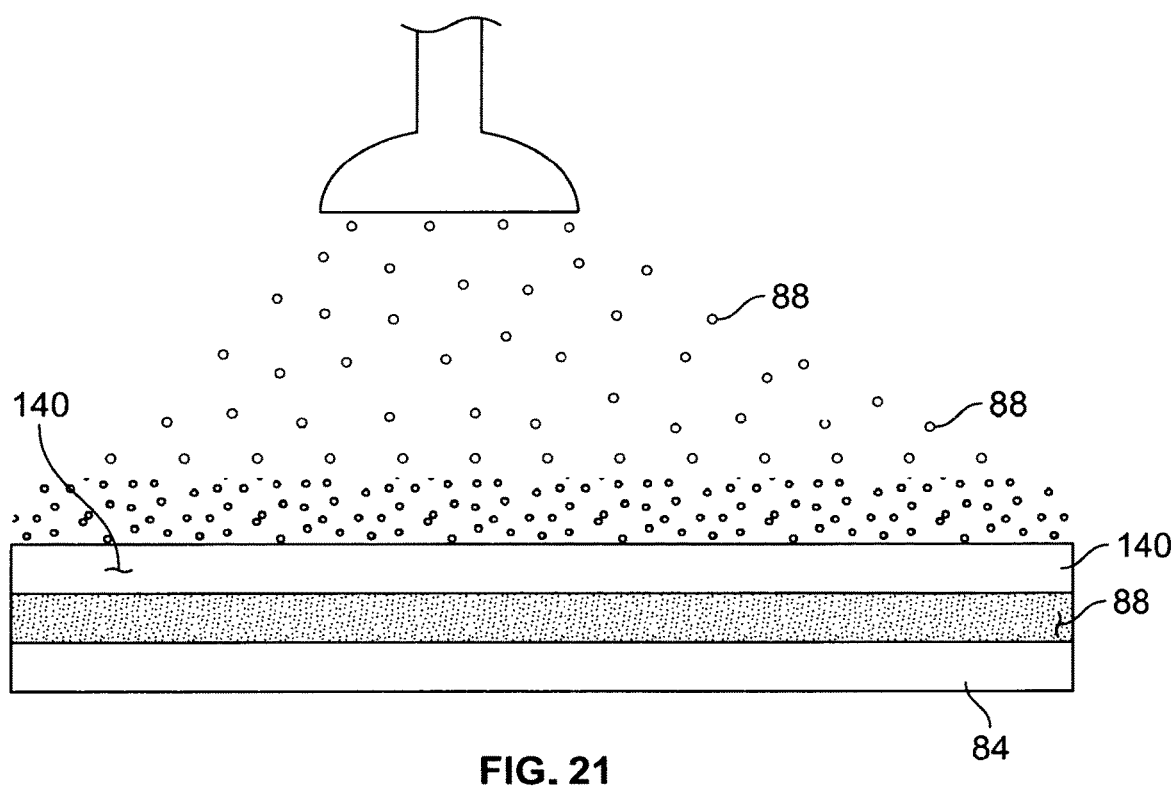
FIG. 21 is a side elevational view of a particulate dispenser sprinkling particulate matter (i.e., a pathogen-deactivating substance) on an intermediate hydrophobic fibrous member after the particulate dispenser had previously sprinkled particulate matter on a fibrous aero-permeable substrate member followed by the intermediate hydrophobic fibrous member being disposed over the previously sprinkled particulate matter, all in the process for producing or forming an embodiment of the pathogen-deactivating assembly.
Figure 22:
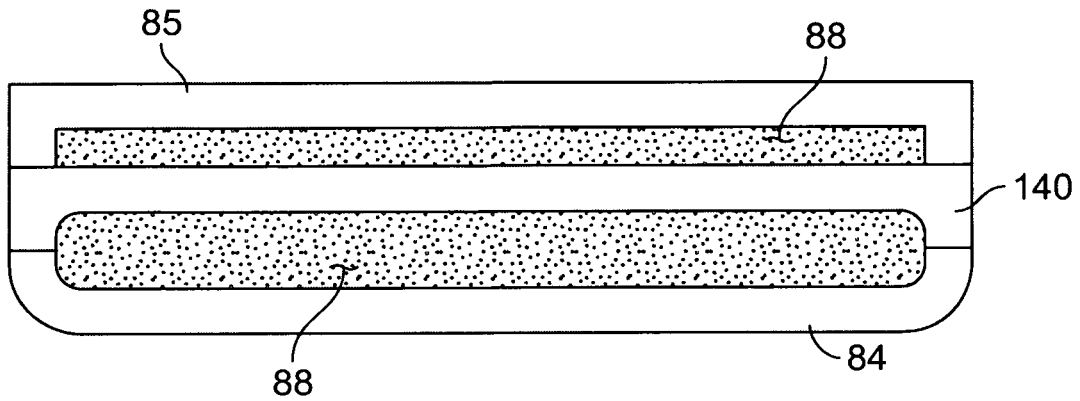
FIG. 22 is a side elevational sectional view of an embodiment of the pathogen-deactivating assembly after the particulate dispenser in FIG. 21 sprinkled particulate matter (i.e., a pathogen-deactivating substance) on the intermediate hydrophobic fibrous member, and after a fibrous aero-permeable superstrate member was imposed over the sprinkled particulate matter and was coupled to the intermediate hydrophobic fibrous member by sealing (preferably sealed by heat) its perimetrical edges to the perimetrical edges of the intermediate hydrophobic fibrous member, and after the perimetrical edges of the fibrous aero-permeable substrate member were sealed to the perimetrical edges of the intermediate hydrophobic fibrous member with previously deposited particulate matter disposed between the fibrous aero-permeable substrate member and the intermediate hydrophobic fibrous member, all producing or forming an embodiment of the pathogen-deactivating assembly.

FIGS. 21 and 22 broadly best illustrates the procedure for encapsulating the particulate matter 88 between substrate 84 and the intermediate fibrous member 140 and between superstrate 85 and the intermediate fibrous member 140. More specifically, initially the particulate dispenser sprinkles particulate matter 88 (e.g., hydrophilic particulate matter with pathogen-deactivating ability or quality) on substrate 84 (e.g., an aero-permeable hydrophilic fibrous member). Subsequently, the intermediate fibrous member 140 is layered or disposed over the sprinkled particulate matter 88 resting on the substrate 84. The particulate dispenser then sprinkles particulate matter 88 on the intermediate fibrous member 140 (as best shown in FIG. 21) followed by disposing or layering the superstrate 85 (e.g., an aero-permeable hydrophilic fibrous member) over the previously sprinkled particulate matter 88.

FIG. 22 is a side elevational sectional view after the particulate dispenser in FIG. 21 sprinkled particulate matter 88 on the intermediate fibrous member 140, and after superstrate 85 was imposed over the sprinkled particulate matter 88 and was coupled to the intermediate fibrous member 140 by sealing (preferably sealed by heat) its perimetrical edges to the perimetrical edges of the intermediate fibrous member 140, and after the perimetrical edges of substrate 84 were sealed (preferably sealed by heat) to the perimetrical edges of the intermediate fibrous member 140 with previously deposited particulate matter 88 disposed between the substrate 84 and the intermediate fibrous member 140. This embodiment of the invention provides two particulate-matter zones 88-88, each possessing deactivating-pathogen characteristics, separated by an aero-permeable intermediate fibrous member 140 which allows air having deactivated pathogens, along with residual pathogen-infected air, to pass therethrough from the first particulate-matter zone 88 into the second particulate-matter zone 88 for deactivating pathogens in the residual pathogen-infected air.

It is well known to those skilled in the art that molecules can be categorized as hydrophobic molecules or hydrophilic molecules according to the response these molecules show to water molecules. Artisans skilled in the art also know that hydrophobic molecules repel water molecules, whereas hydrophilic molecules attract water molecules. The degree or extent to which a molecule or surface attracts water is known as the "hydrophilicity" of that molecule. Some of the most common examples of hydrophilic substances are sugar, salt (e.g., NaCl and KCl), starch, and cellulose. A key difference between hydrophobic and hydrophilic molecules is that hydrophobic molecules are nonpolar whereas hydrophilic molecules are polar. Fibers like rayon, cotton, wool, and linen are naturally hydrophilic, but synthetic fibers such as acrylic, and modacrylic are naturally hydrophobic and have poor water absorbency.

The intermediate member 140 may be any suitable intermediate member for purposes of the present invention. Preferably, the intermediate member 140 comprises hydrophobic characteristics, such as one having poor water/absorbency properties or one naturally repelling water causing droplets to form. More preferably, the intermediate member 140 comprises a fibrous member which includes synthetic fibers that may be any of various man-made textile fibers manufactured through chemical synthesis, as opposed to natural fibers that are directly derived from living organisms, such as plants or fur from animals. Synthetic fibers may include any of those made from natural materials, such as rayon and acetate from cellulose or regenerated protein fibers from zein or casein, as well as fully synthetic fibers, such as nylon or acrylic fibers. Most preferably, the synthetic fibers for the aero-permeable intermediate hydrophobic fibrous member 140 are selected from the group consisting of nylon, acrylic and modacrylic.

Substrate 84 and superstrate 85 for the pathogen-deactivating assembly 30 having the aero-permeable intermediate hydrophobic fibrous member 140 may be manufactured from any suitable material or substance for purposes of embodiments of the present invention, preferably a material or substance which has sufficient aero-permeability allowing pathogen-infected air to pass through and into the particulate matter 88 for deactivating pathogens, and to enable the same air (including deactivated pathogens) to pass out of the pathogen-deactivating assembly 30. Preferably, the fibers or material for producing the substrate 84 and superstrate 85 for the pathogen-deactivating assembly 30 having the aero-permeable intermediate hydrophobic fibrous member 140 comprise hydrophilic characteristics. More preferably, the fibers or materials for manufacturing the substrate 84 and superstrate 85 are selected from the group consisting of rayon, cotton, wool, and linen.

Figure 23:
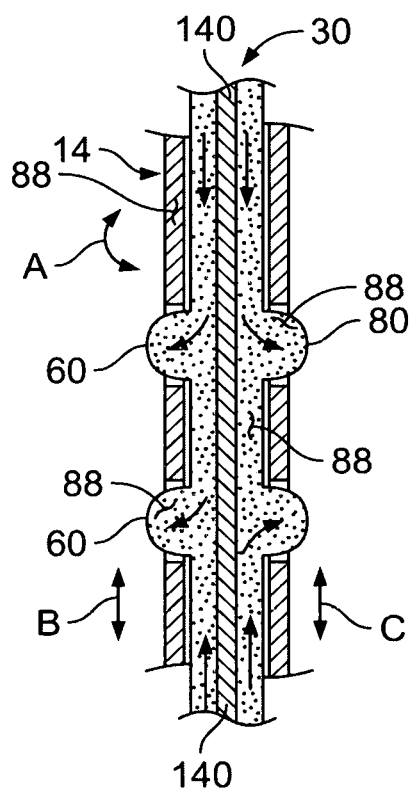
FIG. 23 is a partial sectional view of the outer face member and the inner face member with the pathogen-deactivating assembly (comprising the intermediate hydrophobic fibrous member) being disposed (and sandwiched) between the outer face member and the inner face member, as and while the outer face member and the inner face member are compressing the pathogen-deactivating assembly by moving towards each other (and/or optionally slightly sliding back and forth relatively to each other, or vibrating in combination, or rotating in combination, or moving in any desired or given direction in combination), showing the migration or movement (preferably progressive migration or movement) of the particulate matter within the pathogen-deactivating assembly towards the apertures of the outer face member and the inner face member and the beginning of the formation (preferably progressive formation) of protruding pockets of pathogen-deactivating substance.
Figure 24:
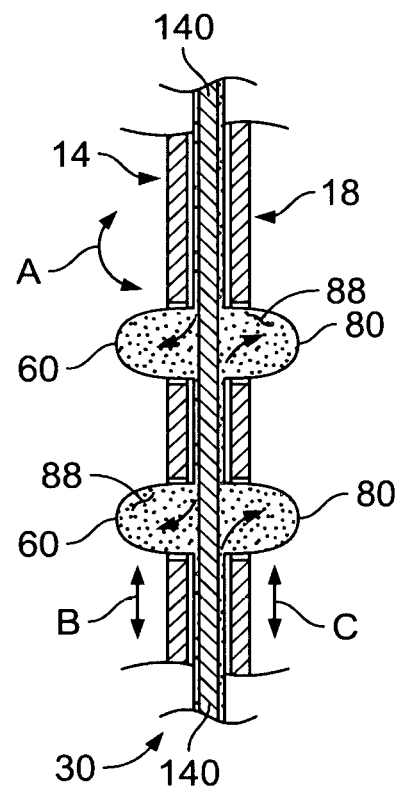
FIG. 24 is a partial sectional view of the outer face member and the inner face member with the pathogen-deactivating assembly (comprising the intermediate hydrophobic fibrous member) being disposed (and sandwiched) between the outer face member and the inner face member, after the outer face member and the inner face member have essentially fully compressed the pathogen-deactivating assembly and have moved a portion of the particulate matter through the apertures of the outer face member and the inner face member, and have formed pockets of pathogen-deactivating substance which protrude through the apertures.

The substrate 84 and superstrate 85 for embodiments of the pathogen-deactivating assembly 30 having the aero-permeable intermediate hydrophobic fibrous member 140 preferably possess sufficient flexibility and elasticity, such that when the outer face member 14 and the inner face member 18 compress the particulate matter 88 (contained within the particulate matter zone between the aero-permeable intermediate hydrophobic fibrous member 140 and substrate 84 and within the particulate matter zone between the aero-permeable intermediate hydrophobic fibrous member 140 and superstrate 85), and/or simultaneously (optionally) with slightly sliding back and forth relatively to each other (as reflected by arrows B and C in FIGS. 23 and 24), or vibrating in combination, or rotating in combination, or moving in any desired or given direction (e.g., shaking) in combination (as reflected by arrows A in FIGS. 23 and 24); the migration or movement of respective particulate matter 88 separated by the aero-permeable intermediate hydrophobic fibrous member 140 occurs towards the respective apertures 46 and 42 of the outer face member 18 and the inner face member 14, to eventually form protruding pathogen-deactivating-substance pockets 60 and 80 separated by the aero-permeable intermediate hydrophobic fibrous member 140 (as illustrated in FIGS. 23 and 24).

It is to be understood that substrate 84 and superstrate 85 may be integrally formed, by-passing two separate elements and forming a continuous outer fibrous bag. (e.g. a tote-bag shaped, a grocery-bag shaped, tea-like bag or pouch shaped) having an internal fibrous partition, preferably a hydrophobic fibrous partition 140 separating the particulate matter 88 into two volumetric sections. The continuous outer fibrous bag would have an opening defined by perimetrical edges which would be sealed or coupled together to fully encapsulate two volumetric portions of particulate matter 88 separated by the hydrophobic fibrous partition 140. Exemplary shapes or images for the continuous outer fibrous bag are shown at https://www.google.com/search?q=grocery+bag&oq=&aqs=chrome.4.69i59i45018.1088913136j0j15&sourceid=chrome&ie=UTF-8, which are fully incorporated herein by reference thereto.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

Additionally, any directional arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context cleanly dictates otherwise. Also, as used in the description herein and throughout the claims that follow, the meaning of "in" includes "in" and "on" unless the context clearly dictates otherwise.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims.

What is claimed is:

1. A method for improving the deactivation of pathogens in a pathogenic aerosol passing through a pathogen-deactivating assembly comprising the steps:
   (a) passing via a user breathing a first pathogenic aerosol matter including a first aqueous fluid comprising water through a first pathogen-deactivating zone of a pathogen-deactivating assembly to deactivate said pathogens and produce a second pathogenic aerosol matter including first residual pathogens and a first residual aqueous fluid comprising said water;
   (b) passing via the user breathing the second pathogenic aerosol matter through a hydrophobic fibrous member in said pathogen-deactivating assembly for removing said water from the first residual aqueous fluid to produce a third pathogenic aerosol matter comprising said first residual pathogens; and
   (c) passing via the user breathing the third pathogenic aerosol matter into and through a second pathogen-deactivating zone of said pathogen-deactivating assembly to deactivate at least a portion of said first residual pathogens in said third pathogenic aerosol matter; wherein said first pathogen-deactivating zone, comprises a first particulate matter being a salt crystal and said second pathogen-deactivating zone comprises a second particulate matter being a salt crystal.

2. The method of claim 1 additionally comprising providing a mask member, and supporting said pathogen-deactivating assembly with said mask member.

3. The method of claim 1 wherein said first particulate matter comprises an alkali metal chloride.

4. The method of claim 1 wherein said first particulate matter comprises an alkali metal chloride and said second particulate matter comprises an alkali metal chloride.

5. The method of claim 1 wherein said first particulate matter comprises said salt crystal including one or more of sodium, potassium, chloride, magnesium, sulfate, ammonium, phosphate, glutamate, tartrate, and the ions of sodium, potassium, chloride, magnesium, sulfate, ammonium, phosphate, glutamate, and tartrate.

6. The method of claim 1 wherein said first particulate matter comprises said salt crystal including one or more of sodium; potassium, chloride, magnesium, sulfate, ammonium, phosphate, glutamate, tartrate, and the ions of sodium, potassium, chloride, magnesium, sulfate, ammonium, phosphate, including one or more of sodium, potassium, chloride, magnesium, sulfate, ammonium, phosphate, glutamate, tartrate, and the ions of sodium, potassium, chloride, magnesium, sulfate, ammonium, phosphate, glutamate, and tartrate.

7. The method of claim 1 wherein said first particulate matter comprises first particles having a total surface area ranging from about 20.00 $m^2/g$ to about 300.00 $m^2/g$.

8. The method of claim 1 wherein said first particulate matter comprises first particles having a total surface area ranging from about 20.00 $m^2/g$ to about 300.00 $m^2/g$, and said second particulate matter comprises second particles having a total surface area ranging from about 20.00 $m^2/g$ to about 300.00 $m^2/g$.

9. The method of claim 1 wherein said first particulate matter is selected from the group consisting of sodium chloride, potassium chloride, and mixtures thereof, and includes first particles having a total surface area ranging from about 100.00 $m^2/g$ to about 300.00 $m^2/g$.

10. The method of claim 1 wherein said first particulate matter is selected from: the group consisting of sodium chloride, potassium chloride, and mixtures thereof, and includes first particles having a total surface area ranging from about 100.00 $m^2$/g to about 300.00 $m^2$/g; and said second particulate matter is selected from the group consisting of sodium chloride, potassium chloride, and mixtures thereof, and includes second particles having a total surface area ranging from about 100.00 $m^2$/g to about 300.00 $m^2$/g.

11. The method of claim 1 additionally comprising providing a mask member, and supporting said pathogen-deactivating assembly with said mask member; and said first particulate matter comprises first particles of sodium chloride having a total surface area ranging from about 100.00 $m^2$/g to about 300.00 $m^2$/g; and said second particulate matter comprises second particles of sodium chloride having a total surface area ranging from about 100.00 $m^2$/g to about 300.00 $m^2$/g.

12. The method of claim 1 wherein said first pathogen-deactivating zone comprises the first particulate matter comprising first hydrophilic particles having a total surface area ranging from about 30.00 $m^2$/g to about 100.00 $m^2$/g; and said second pathogen-deactivating zone comprises second particulate matter comprising second hydrophilic particles having a total surface area ranging from about 30.00 $m^2$/g to about 100.00 $m^2$/g.

13. The method of claim 12 additionally comprising providing a mask member, and supporting said pathogen-deactivating assembly with said mask member.

14. The method of claim 1 wherein said hydrophobic fibrous member comprises a synthetic fiber selected from the group consisting of nylon, acrylic and modacrylic.

15. The method of claim 1 additionally comprising providing a mask member, and supporting said pathogen-deactivating assembly with said mask member; and encapsulating said first particulate matter and said second particulate matter with a fibrous member prior to said passing step (a).

16. The method of claim 1 additionally comprising providing a mask member; supporting the pathogen-deactivating assembly with the mask member; and donning the mask member supporting the pathogen-deactivating assembly such that the pathogen-deactivating assembly is in a position to deactivate said pathogens in the pathogenic aerosol when the person wearing the mask inhales causing said passing steps (a), (b) and (c) and the deactivation of said pathogens.

* * * * *